(12) United States Patent
Schmidt et al.

(10) Patent No.: US 7,963,106 B2
(45) Date of Patent: Jun. 21, 2011

(54) METHOD AND APPARATUS FOR THE DEFINED REGENERATION OF SOOTY SURFACES

(75) Inventors: Ralf Schmidt, Gerlingen (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1285 days.

(21) Appl. No.: 11/145,472

(22) Filed: Jun. 3, 2005

(65) Prior Publication Data

US 2005/0279084 A1  Dec. 22, 2005

(30) Foreign Application Priority Data

Jun. 18, 2004  (DE) .......................... 10 2004 029 524

(51) Int. Cl.
*F01N 3/00* (2006.01)
(52) U.S. Cl. .......................................... 60/295; 60/275
(58) Field of Classification Search .................. 60/295, 60/275; 204/424
See application file for complete search history.

(56) References Cited

U.S. PATENT DOCUMENTS

| | | | | |
|---|---|---|---|---|
| 5,263,317 | A * | 11/1993 | Watanabe et al. ............... | 60/275 |
| 6,038,854 | A * | 3/2000 | Penetrante et al. ............. | 60/297 |
| 6,474,060 | B2 * | 11/2002 | Khair .............................. | 60/275 |
| 6,660,068 | B1 * | 12/2003 | Garner et al. ................... | 95/283 |
| 6,938,409 | B2 * | 9/2005 | Birckigt et al. ................. | 60/275 |
| 7,258,723 | B2 * | 8/2007 | Crawley et al. ................. | 95/5 |
| 2002/0013666 | A1 | 1/2002 | Schmid | |
| 2004/0079631 | A1 | 4/2004 | Birckigt et al. | |
| 2005/0039441 | A1 * | 2/2005 | Kakinohana et al. ........... | 60/275 |
| 2008/0178657 | A1 * | 7/2008 | Komatsu et al. ............. | 73/23.33 |

FOREIGN PATENT DOCUMENTS

| | | |
|---|---|---|
| DE | 33 04 548 | 8/1984 |
| DE | 197 17 890 | 4/1999 |
| DE | 100 57 862 C1 | 2/2002 |
| DE | 10133384 | 1/2003 |
| JP | 09329015 | 12/1997 |
| WO | 0242615 | 5/2002 |

OTHER PUBLICATIONS

Plasma Exhaust Treatment, DieselNet Technology Guide, WYSIWYG://90/HTTP://WWW.DIESELNET.COM/TECH/PLASMA.HTML, 1999.

* cited by examiner

*Primary Examiner* — Thomas E Denion
(74) *Attorney, Agent, or Firm* — Michael J. Striker

(57) ABSTRACT

In a method and an apparatus for the defined regeneration of a sooty surface, in particular a ceramic sensor surface, in which the soot particles adhering to the surface are burned off by a dielectrically hindered discharge by of a discharge device, power of the dielectrically hindered discharge is set such that a higher rate of removal of the soot particles than their rate of deposition on the surface is effected, after the regeneration phase, the remaining soot deposit is detected by a measuring device mounted on the surface, wherein an undefined state of the sensor surface does not occur, and the discharge device and the measuring device may be mounted very compactly on one or two ceramic substrate elements.

8 Claims, 2 Drawing Sheets

METHOD AND APPARATUS FOR THE DEFINED REGENERATION OF SOOTY SURFACES

CROSS-REFERENCE

The invention described and claimed hereinbelow is also described in DE 10 2004029524.7, filed Jun. 18, 2004. This German Patent Application, whose subject matter is incorporated here by reference, provides the basis for a claim of priority of invention under 35 U.S.C. 119 (a)-(d).

BACKGROUND OF THE INVENTION

The present invention relates to a method and an apparatus for the defined regeneration of sooty surfaces, in particular of ceramic sensor surfaces.

In the course of environmental efforts to reduce the expulsion of soot from diesel engines, it becomes necessary to be able to determine the concentration of soot particles in the exhaust gas in a simple way. In particular, monitoring the soot content downstream of a diesel particle filter (DPF) during driving makes sense. For monitoring regeneration, moreover, the loading of a diesel particle filter must be predicted, for the sake of achieving high system security.

For determining the soot concentration in the exhaust gas of internal combustion engines, a sensor with a device for detecting soot particles can be mounted in the exhaust pipe.

From German Patent Disclosure DE 33 04 548 A1, a sensor is known that has electrodes on a nonconductive surface. The soot concentration can be derived from the conductivity, or the change in conductivity from soot deposition on the creep current surface located between the electrodes.

This measuring method is equivalent to a cumulative measurement principle, and the sooty sensor surface must therefore be freed of the conductive soot particles from time to time. For regeneration of the sooty surface, it is proposed that a high voltage be applied between the electrodes, in order to burn off the soot particles by way of the flow of current.

One disadvantage of the procedure proposed above arises from the fact that the electrodes themselves can be damaged by the thermal and electrical load, for instance from spark development between the electrodes, and the electromagnetic compatibility (EMC) of this method is a problem.

Moreover, especially with sensors with a ceramic multi-layer construction, the integration of a heater and a temperature measuring element by thick-film technology suggests itself for regenerating the sensor surface. The regeneration is then done by simple heating to above the soot burnoff temperature. However, in this method as well, there is the disadvantage that because of the heating and cooling of the sensor and its thermal inertia, situations arise in which the soot deposition occurs in an undefined way and is difficult to monitor. In particular, during regeneration above 650° C., no soot is deposited; that is, during this phase, the sensor is incapable of making measurements.

As a result, it is impossible to draw a conclusion about a deposition rate in the regeneration phase, or the deposition rate on the heated sensor surface, regardless of the actual concentration of soot particles in the exhaust system, is equal to zero. At the same time, controlled adjustment of the rate of removal of the soot particles is made more difficult by the kind of method described above. Another possible way of freeing a sooty surface of soot is to burn off the soot particles by means of a dielectrically hindered discharge (DHD).

In a DHD, because a dielectric is positioned between the discharge electrodes, the development of a spark or an arc in the plasma upon application of a high voltage is suppressed, resulting in a nonthermal plasma. Typically, a DHD is excited with pulsating or alternating voltage. Gas discharges ignited in alternation in opposite directions break down the charge of the dielectric again before it can be built up significantly. Significant heating of the gas therefore does not occur.

If soot particles are conducted through a nonthermal plasma, radicals form and trip plasma-chemical reactions at the soot surfaces, and the soot particles become oxidized. Using the DHD for cleaning sooty surfaces is known per se.

In German Patent DE 100 57 862 C1, for instance, a method and an arrangement for reducing carbon-containing particle emissions from diesel engines is proposed in which the particles contained in the exhaust gas are deposited on filter surfaces, and the deposited particles are oxidized for the sake of regenerating the filter. The regeneration is done by means of nonthermal, electrical surface sliding discharges at the surfaces occupied by particles. In principle, the regeneration can be done either continuously or cyclically. In the case of a continuous regeneration, it is proposed that the requisite mean plasma capacity be regulated in accordance with the filter temperature, soot emissions, or the exhaust gas counterpressure, and in the case of a cyclical regeneration, by means of the exhaust gas counterpressure and the filter temperature. The goal of these concepts is to enable operating the plasma with as little expenditure of energy as possible. In particular for this purpose, it is provided that the filter ceramic be doped with catalytic materials.

Another method and an apparatus for plasma-supported decomposition of soot are known from German Patent DE 197 17 890 C1. Here as well, the filtered-out soot particles are made to react with oxygen on the principle of the dielectrically hindered discharge. In this case, at least one porous discharge electrode is especially provided in the flow course of the exhaust gas and is designed such that it is permeable to gaseous components but acts as a filter for the soot particles and traps them. The operation of the DHD can be done in a regulated way, and the voltage supply of the discharge electrodes can be switched on or off in response to the charge state of the electrodes with particles, which is ascertained by means of a sensor.

In the methods known from the prior art, the goal is to clean diesel exhaust gases per se, that is, to decompose soot particles that are present in exhaust gases. For this purpose, filter bodies are mounted in the flow course of the exhaust gas, where the soot particles are trapped and burned off by means of a DHD. It is therefore neither necessary nor contemplated, in the methods described until now, that the surface be kept in a defined sooty state.

SUMMARY OF THE INVENTION

Accordingly, it is an object of the present invention to provide method and apparatus for the defined regeneration of sooty surfaces, which are further improvements of the existing methods and apparatus.

In keeping with these objects and with others which will become apparent hereinafter, one feature of the present invention resides, briefly stated, in a method for defined regeneration of a sooty surface, in particular of a ceramic sensor surface of a first substrate element, comprising the steps of burning off soot particles adhering to the surface by a dielectrically hindered discharge by means of a discharge device; providing in the discharge device a first and a second discharge electrode and a dielectric located between the discharge electrodes; setting wherein setting a power of the electrically hindered discharge is set such that a higher rate of removal of the soot particles than their rate of deposition of the surface (30) is effected; and after a predetermined length of time, switching of the electrically hindered discharge; and detecting a remaining soot deposit by means of a measuring device mounted on the surface.

The method of the invention for the defined regeneration of sooty surfaces, in particular ceramic sensor surfaces, has the advantage that a method is furnished in which the deficiencies described above, such as aging of the electrodes, EMC problems, and above all the undefined states for the soot deposition in the regeneration phase are eliminated or at least greatly reduced.

The method of the invention can in particular be employed to monitor a diesel particle filter (DPF) in the diesel exhaust system downstream of a DPF.

Another feature of the present invention resides in an apparatus for the defined regeneration of a sooty surface, in particular a ceramic sensor surface of a first substrate element, comprising a measuring device for detecting soot particles on the surface; a discharge device, having a first and a second discharge electrode and a dielectric, located between the discharge electrodes, for burning off the soot particles adhering to the surface by means of a dielectrically hindered discharge; and means for setting a power of the electrically hindered discharge such that a higher rate of removal of the soot particles than their rate of deposition of the surface is effected.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
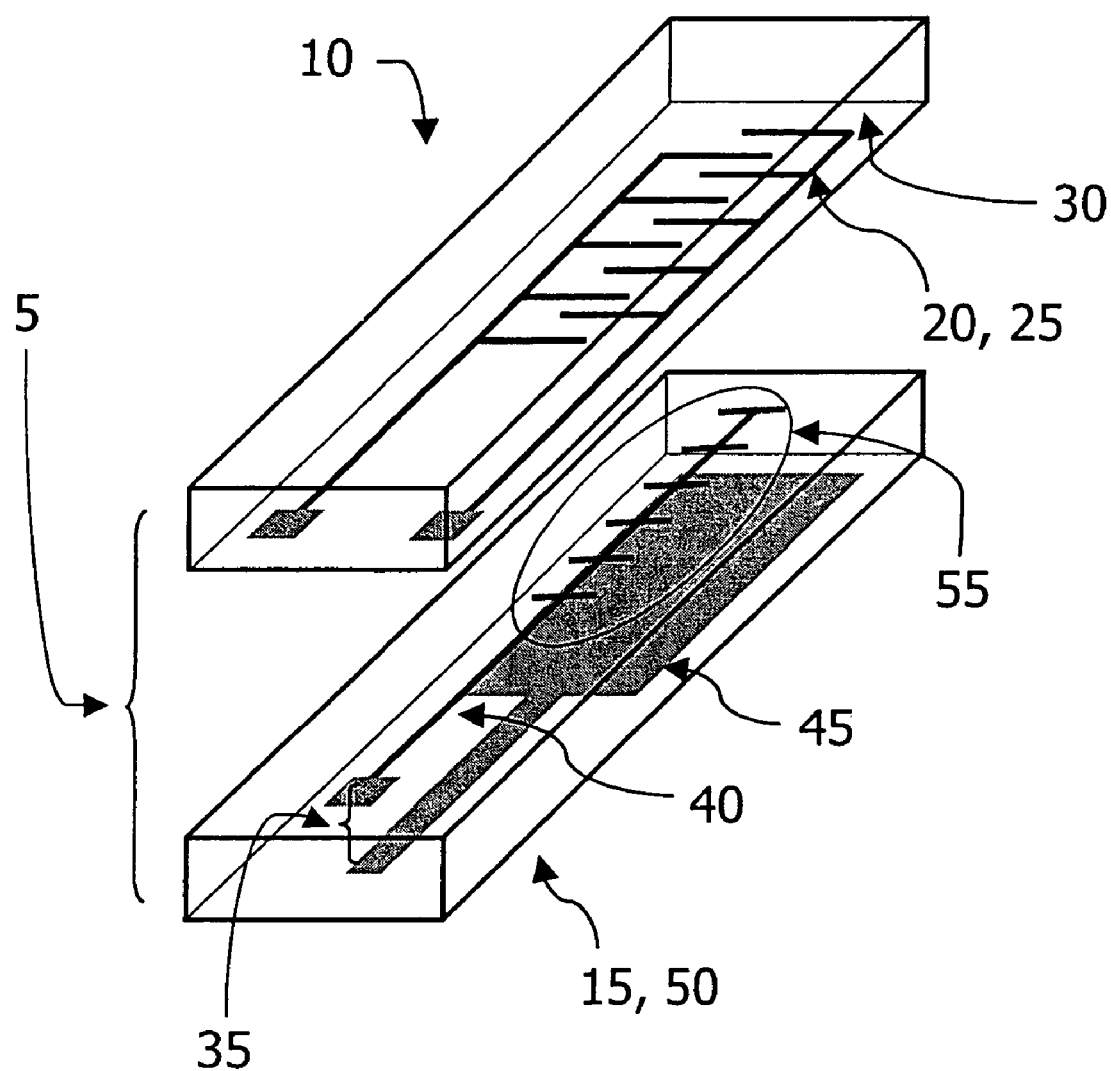
FIG. 1 is a perspective view of a first exemplary embodiment of an apparatus for the defined regeneration of sooty surfaces, having a first and a second substrate element.

In a first exemplary embodiment shown in FIG. 1, the particle sensor 5 comprises a first ceramic substrate element 10 and a second ceramic substrate element 15. The two substrate elements 10, 15 are located parallel to one another, with an interstice between them. The measuring device 20 required for detecting soot particles is mounted on the face 30 of the first substrate element 10 that faces toward the second substrate element 15. Advantageously, the measuring device 20 is an interdigital electrode structure 25. If soot particles are deposited on the sensor surface, the impedance of the interdigital electrode structure 25 changes.

According to the invention, the sooty surface 30 is regenerated by means of a dielectrically hindered discharge (DHD). For operating the DHD 55, a discharge device 35 that has two discharge electrodes 40, 45 is provided on the second substrate element 15. The first and the second discharge electrode 40, 45 are mounted on the top and bottom side, respectively, of the second, ceramic substrate element 15, so that the space between them is filled with part of the substrate element 15 and thus acts as a dielectric 50.

In the exemplary embodiment, the first discharge electrode 40 has an antenna-like structure, which is formed of a long, electrically conductive base line with a plurality of short transverse lines, parallel to one another and perpendicular to the base line. Care is therefore taken to provide a favorable geometry of the discharge electrodes 40, 45, because the discharge volume of the DHD 55 is dependent on that geometry.

With the DHD 55 initially off, soot is deposited both on the discharge electrodes 40, 45 and on the interdigital electrode structure 25. If a pulsating or alternating high voltage is then applied to the discharge electrodes 40, 45, a nonthermal plasma ignites. Advantageously, whichever discharge electrode 40 has a lesser spacing from the measuring device 20 is applied to ground, to avoid premature crosstalk and spark formation. The DHD 55 here burns on the side having the first discharge electrode 40. The resultant discharge volume of the DHD 55 extends right up to the face 30 having the measuring device 20.

According to the invention, the power of the DHD 55 is set such that the soot is burned off at a predetermined, known removal rate. While the DHD 55 is burning, soot can nevertheless still be deposited, as experiments have confirmed. Accordingly, a regeneration of the sooty surface 30 takes place only whenever the removal rate is higher than the deposition rate. The removal rate is therefore selected via the power of the DHD 55 in such a way that it is higher than the deposition rate. After a predetermined length of time, the DHD 55 is switched off, and the remaining soot deposit is detected by means of the measuring device 20 mounted on the sooty surface 30.

Since the state of the surface 30 can be determined immediately before and immediately after the regeneration phase with the aid of the measuring device 20, and the removal rate during the regeneration phase is adjustable, the new deposition can be ascertained during the regeneration phase. It is thus assured that in this regeneration method, not only full regeneration but also partial regeneration are made possible.

Moreover, in contrast to the methods known until now, undefined states do not occur, since on the one hand the soot concentrations that occur during the regeneration are detected as well, and on the other, the sensor can be switched over directly from regeneration to measurement and vice versa. Arbitrarily short regeneration and measurement cycles allow practically permanent monitoring.

A further embodiment of the particle sensor for performing the method of the invention will now be explained with the aid of the arrangement shown in FIG. 2.

Figure 2:
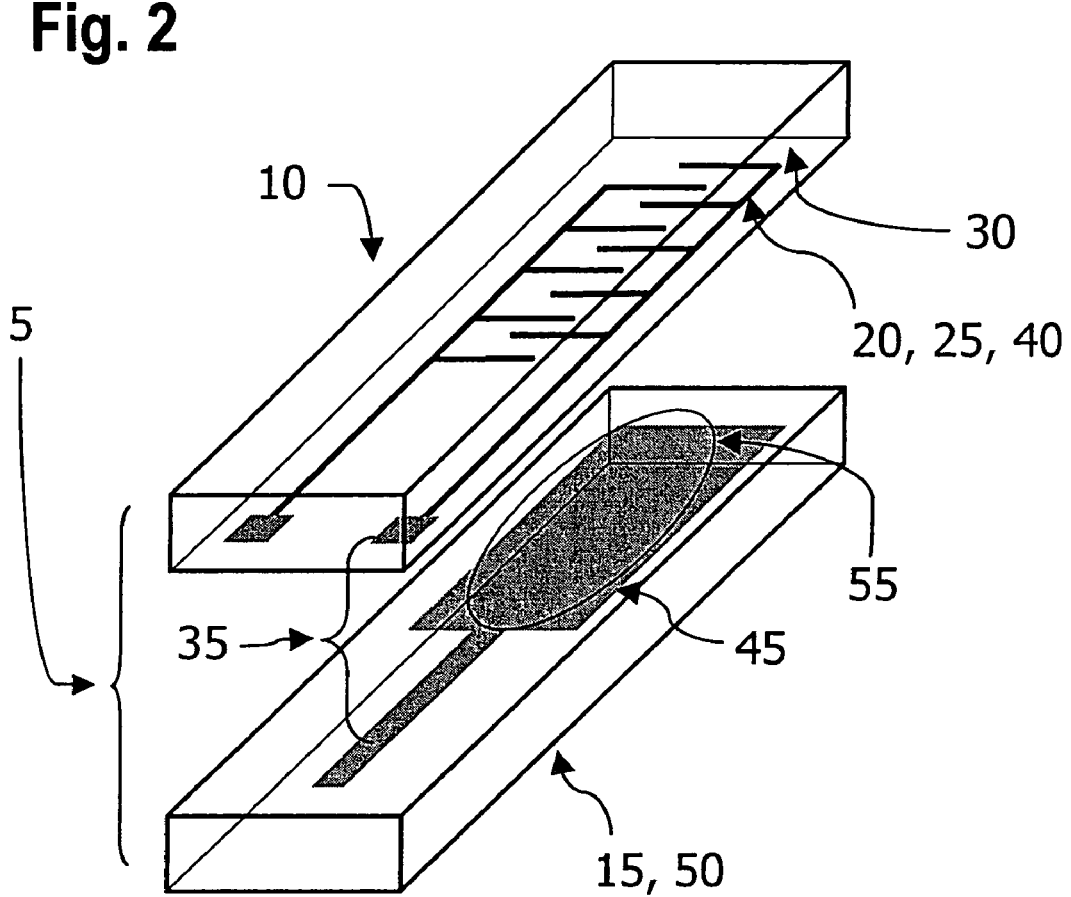
FIG. 2 is a perspective view of a second exemplary embodiment of an apparatus for the defined regeneration of sooty surfaces, having a first and a second substrate element.

FIG. 2, as in the first exemplary embodiment, shows a particle sensor 5 that comprises two substrate elements 10, 15. However, unlike the first exemplary embodiment, the measuring device 20 and the discharge device 35 are not located separately from one another on two substrate elements 10, 15; instead, there is an integrated form: The interdigital electrodes 25 serve not only as the measuring device 20 but also as the first discharge electrode 40.

The second discharge electrode 45 is now located on the side of the second substrate element 15 facing toward the face 30 having the measuring device 20, and the discharge electrode 45 is covered by a part of the second substrate element 15. As a result, it is attained that a dielectric 50 is located between the discharge electrodes 40, 45. Ground is advantageously applied to the measuring device 20, that is, to the first discharge electrode 40.

Figure 3:
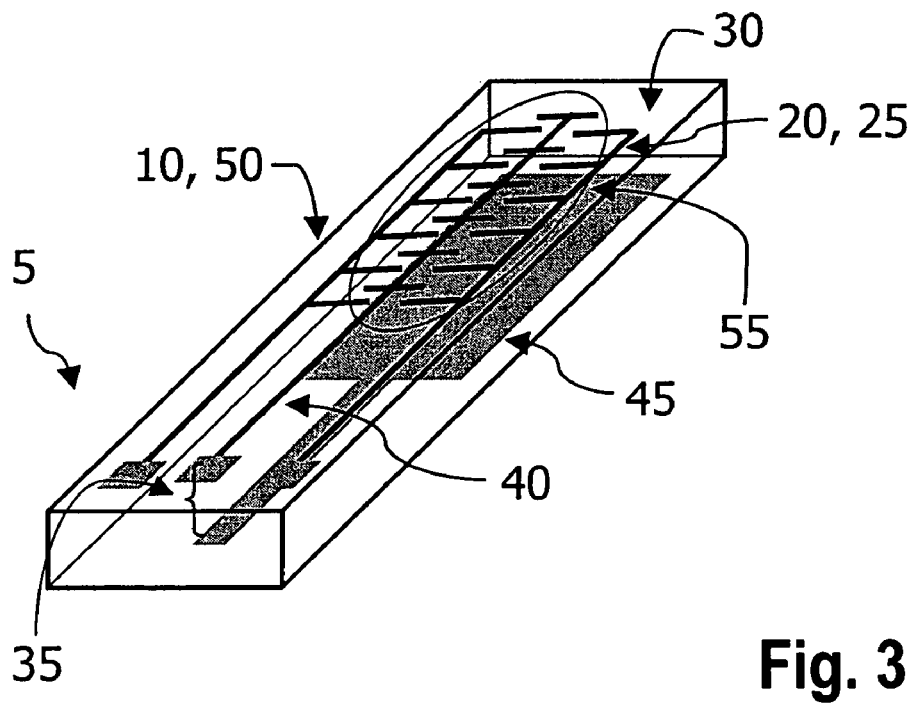
FIG. 3, again in perspective, shows a third exemplary embodiment of an apparatus for the defined regeneration of sooty surfaces, having a single substrate element.

Finally, FIG. 3 shows an example for integration of a measuring device 20 and a discharge device 35 on a single substrate element 15. The measuring device 20 is mounted together with the first discharge electrode 40 on one surface 30 of the substrate element 15, while the second discharge electrode 45 is mounted on the other side of the substrate element 15. Once again, part of the substrate element 15 is located as a dielectric 50 between the discharge electrodes 40, 45, and ground is advantageously applied to the first discharge electrode 40. Once again, the first discharge electrode 40 can be dispensed with, if the measuring device 20 takes on its function in addition.

In summary, all the exemplary embodiments described of the apparatus for the defined regeneration of sooty surfaces have a very compact structure, so that their use is made possible not only in the exhaust system of a motor vehicle but wherever monitoring of the soot concentration in a space-saving way is necessary or desired.

It will be understood that each of the elements described above, or two or more together, may also find a useful application in other types of methods and constructions differing from the types described above.

While the invention has been illustrated and described as embodied in a method and an apparatus for the defined regeneration of sooty surfaces, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A method for defined regeneration of a sooty surface, in particular of a ceramic sensor surface of a first substrate element, comprising the steps of burning off soot particles adhering to the surface by a dielectrically hindered discharge by means of a discharge device; providing in the discharge device a first and a second discharge electrode and a dielectric located between the discharge electrodes; setting a power of the electrically hindered discharge such that a higher rate of removal of the soot particles than their rate of deposition of the surface is effected; after a predetermined length of time, switching off the electrically hindered discharge; and detecting a remaining soot deposit by means of a measuring device mounted on the surface.

2. An apparatus for the defined regeneration of a sooty surface, in particular a ceramic sensor surface of a first substrate element, comprising a measuring device for detecting soot particles on the surface; a discharge device, having a first and a second discharge electrode and a dielectric, located between the discharge electrodes, for burning off the soot particles adhering to the surface by means of a dielectrically hindered discharge; and means for setting a power of the electrically hindered discharge such that a higher rate of removal of the soot particles than their rate of deposition of the surface is effected.

3. The apparatus as defined in claim 2, wherein the measuring device for detecting soot particles on the ceramic surface of the first substrate element are interdigital electrodes.

4. The apparatus as defined in claim 2, wherein the measuring device is mounted on the first substrate element, and at least one of the two discharge electrodes is mounted on a second substrate element, and the first substrate element is located such that its surface having the measuring device faces toward the second substrate element.

5. The apparatus as defined in claim 2, wherein the measuring device and the discharge electrodes are mounted on a single substrate element.

6. The apparatus as defined in claim 2, wherein the measuring device is simultaneously embodied as one of the two discharge electrodes.

7. The apparatus as defined in claim 2, wherein the dielectric is formed at least in part by an element selected from the group consisting of the first substrate element, the second substrate element, and both.

8. The apparatus as defined in claim 2, wherein one of the discharge electrodes that has a lesser spacing from the measuring device is connected to ground.

* * * * *